United States Patent [19]

Nugent

[11] 4,140,108
[45] Feb. 20, 1979

[54] BLOOD COLLECTION ASSEMBLY

[75] Inventor: Edward L. Nugent, North Caldwell, N.J.

[73] Assignee: Becton, Dickinson and Company, Rutherford, N.J.

[21] Appl. No.: 823,415

[22] Filed: Aug. 10, 1977

[51] Int. Cl.² .............................................. A61B 5/14
[52] U.S. Cl. ............................. 128/2 F; 128/DIG. 5
[58] Field of Search ............ 128/2 F, DIG. 5, 218 R, 128/218 N, 221, 276

[56] References Cited

U.S. PATENT DOCUMENTS

| 3,877,465 | 4/1975 | Miyake | 128/2 F |
| 3,906,930 | 9/1975 | Guerra | 128/2 F |

FOREIGN PATENT DOCUMENTS

| 599394 | 10/1959 | Italy | 128/DIG. 5 |
| 528471 | 10/1940 | United Kingdom | 128/DIG. 5 |

Primary Examiner—John D. Yasko
Attorney, Agent, or Firm—Kane, Dalsimer, Kane, Sullivan and Kurucz

[57] ABSTRACT

The disclosure is of an assembly for the collection of blood from a mammalian blood vessel. The assembly comprises a flexible tube having needle cannulas mounted on each end. One of the needle cannulas is threadably secured to a holder member for holding a blood collection container. The assembly of the invention makes possible blood sampling regardless of the orientation of the mammal from whom the blood is being collected.

6 Claims, 13 Drawing Figures

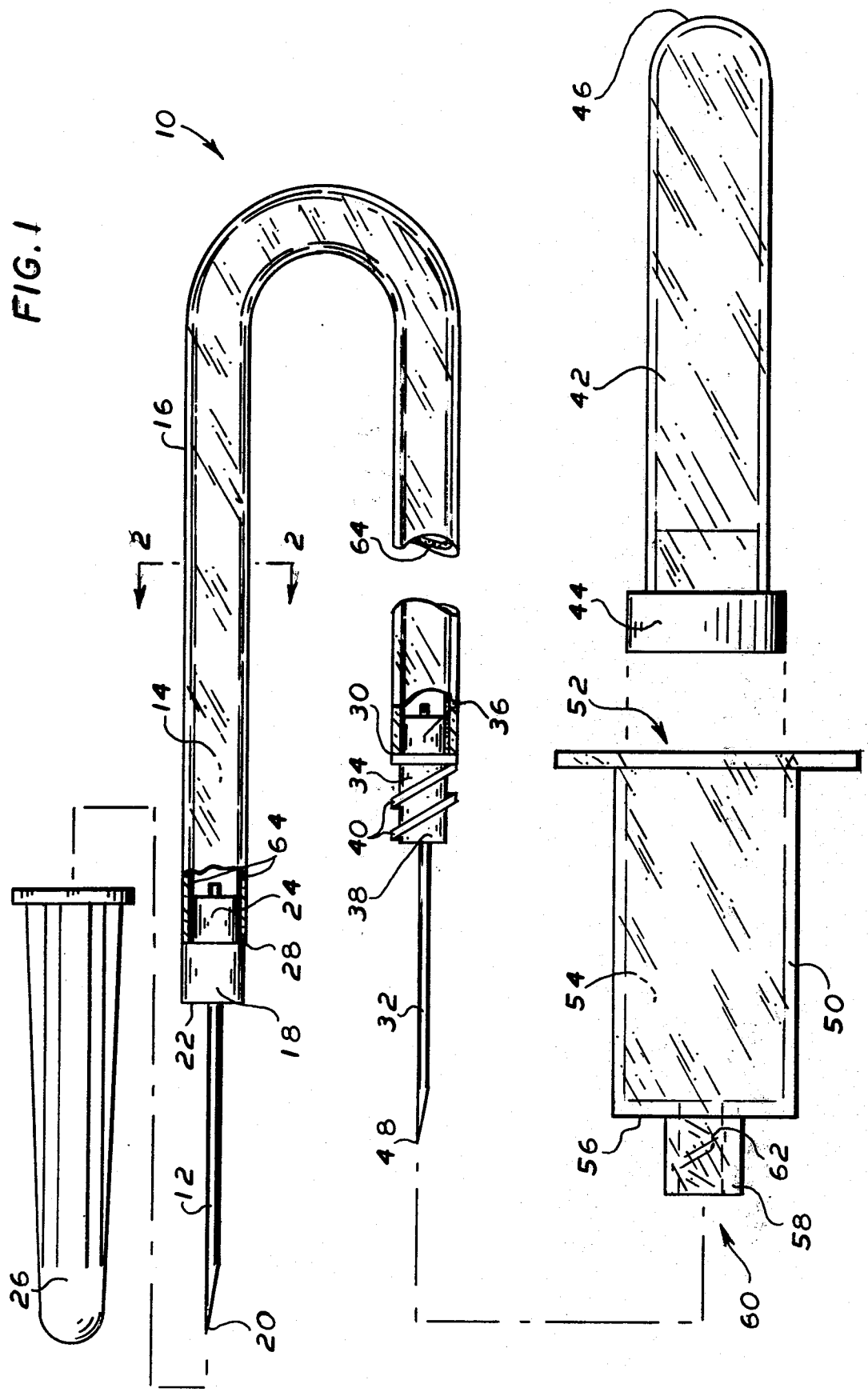

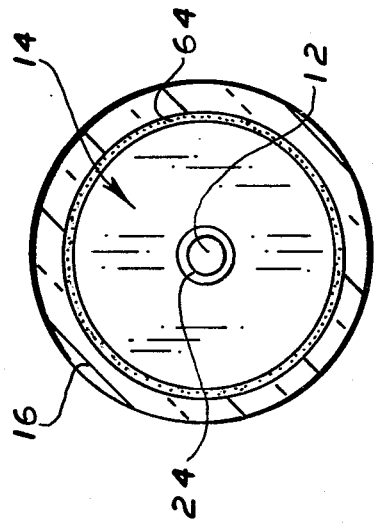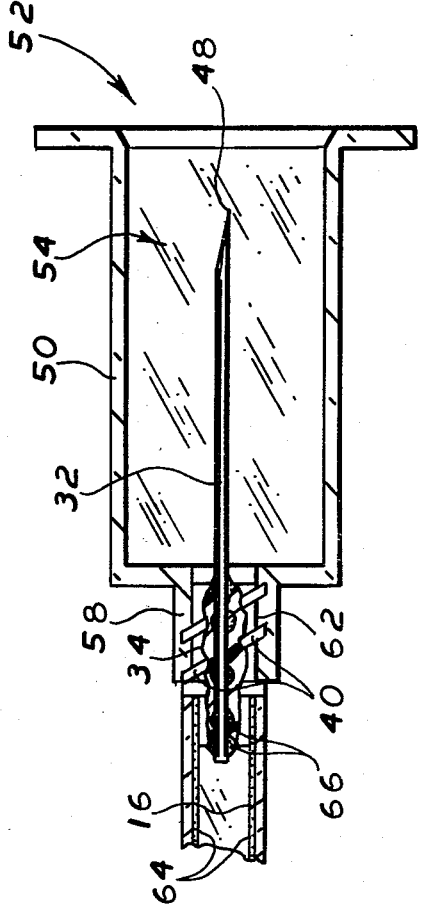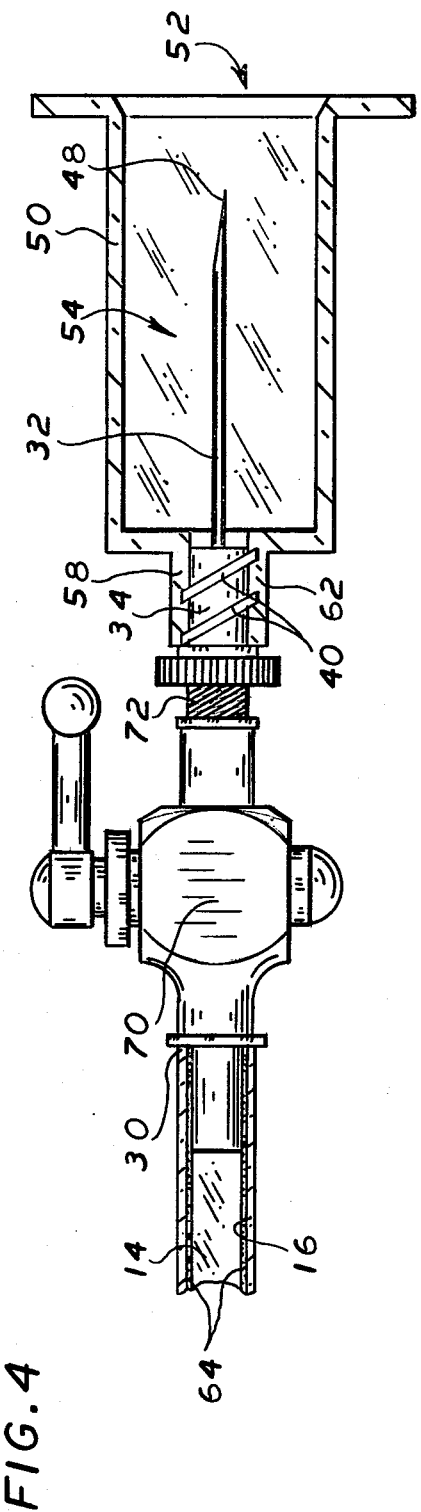

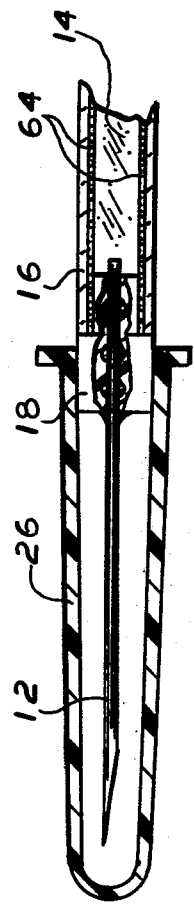
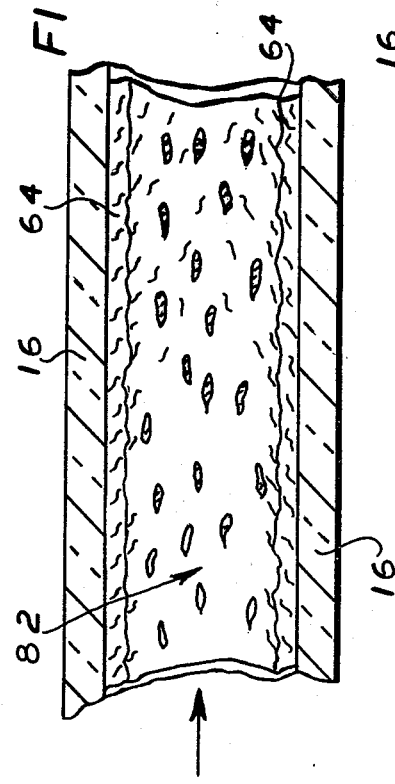
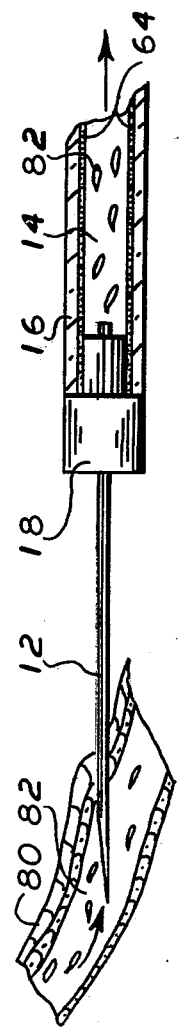
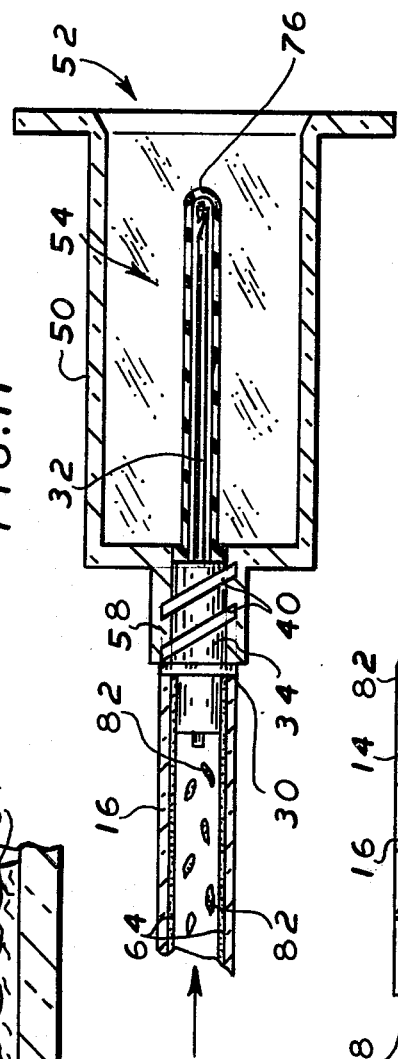
FIG. 8
FIG. 10
FIG. 11
FIG. 9

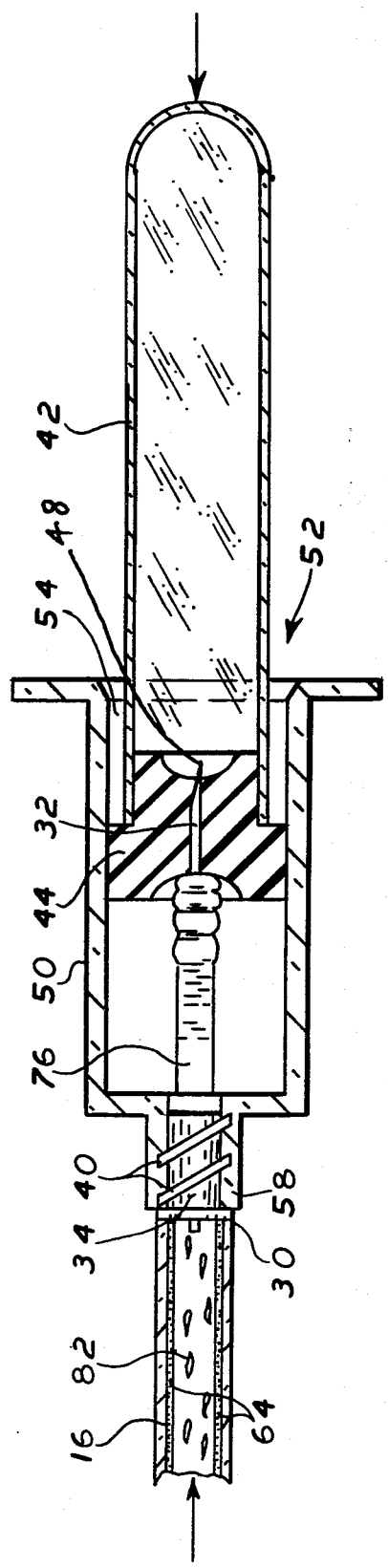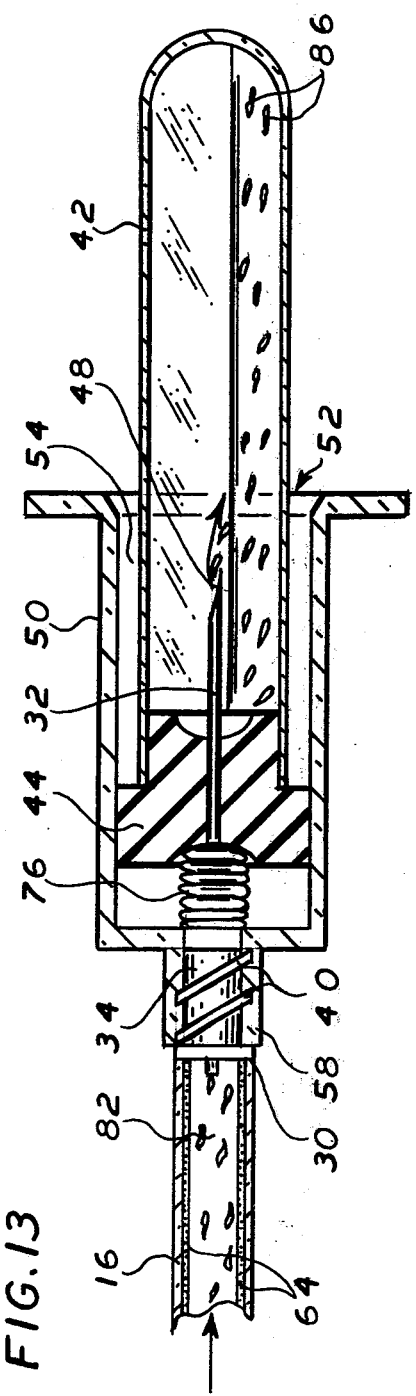

4,140,108

BLOOD COLLECTION ASSEMBLY

BACKGROUND OF THE INVENTION

1. Field of the Invention

The invention relates to medical-surgical instruments and more particularly relates to apparatus for removing blood from a mammalian blood vessel.

2. Brief Description of the Prior Art

The art is replete with descriptions of blood collection assemblies. Representative of prior art assemblies are those described in U.S. Pat. Nos. 2,290,857; 2,847,995; 3,494,351; 3,494,352; 3,734,080; 3,848,579; 3,874,367; and 3,886,930.

The assembly of the present invention is particularly advantageous over prior art assemblies in that it provides a great deal of flexibility to the operator in removing blood from a mammalian blood vessel. The patient may be oriented in any particular fashion and the blood collection container need not be in the immediate vicinity of the mammal. In addition, a number of components of the assembly of the invention may be reused a plurality of times, which was not always possible with the prior art assemblies.

SUMMARY OF THE INVENTION

The invention comprises an assembly for the collection of blood from a mammalian blood vessel, which comprises;

- a first needle cannula adapted to puncture said vessel and carry blood therefrom;
- a first cannula hub having a first end and a second end, within which said needle cannula is mounted, the needle cutting edge being proximal to said first end and distal to said second end;
- a length of flexible tube having a first end and a second end, the first end of which is attached to the second end of said hub and the bore of said tube being in open communication with the bore of said needle cannula;
- a second cannula hub having a first end connected to the second end of said tube and a second end bearing threads;
- a second needle cannula adapted to penetrate a cannula penetrable closure in a sealed vacuum bottle for collecting blood, mounted in said second hub with the penetration point proximal to the second end of said second hub and distal to the first end of said second hub; and
- a holder which comprises a tubular member having an open first end adapted to receive a blood collection container and hold it and a closed second end formed with a hub, said holder hub having an axial bore therethrough communicating with the bore of said tubular member, said axial bore bearing threads adapted to engage the threads of said second cannula hub, said holder being removably mounted on the second end of the cannula hub by the engagement of said threads.

BRIEF DESCRIPTION OF THE DRAWINGS

FIG. 1 is an isometric view of an embodiment assembly of the invention shown disassembled.

FIG. 2 is a cross sectional view along lines 2—2 of FIG. 1.

FIG. 3 is a cross-sectional side elevation of the container holder component of the assembly of the invention shown assembled to the rest of the assembly of the invention.

FIG. 4 shows an alternate structure of the assembly of the invention, including a valve means.

FIG. 8 is a cross-sectional side elevation in part of the blood vessel piercing end of the assembly of the invention.

FIG. 9 is a view of the end of the assembly of the invention shown in FIG. 8, showing introduction into a mammalian blood vessel and initial flow of blood.

FIG. 10 is a cross-sectional side elevation of a portion of the tubular component of the assembly of the invention, showing the flow of blood therein following introduction of blood.

FIG. 11 is a cross-sectional, in part side elevation of the terminal portion of the assembly of the invention showing the flow of blood.

FIG. 12 shows the insertion of a blood collection container into the terminal end or holder of the assembly of the invention.

FIG. 13 is a view as seen in FIG. 12 but with complete insertion of a blood collection container into the holder component of the assembly of the invention.

DETAILED DESCRIPTION OF THE PREFERRED EMBODIMENTS OF THE INVENTION

Figure 5:
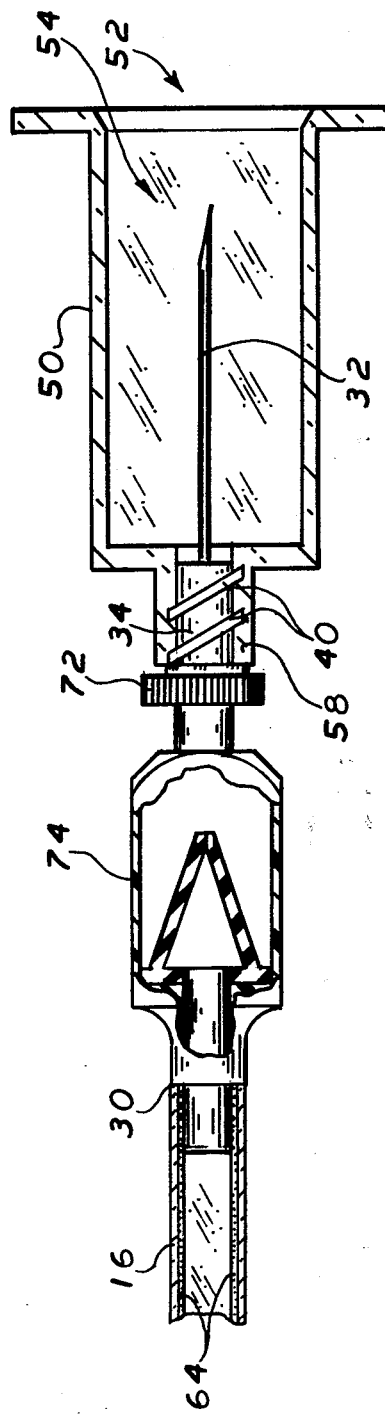
FIG. 5 is a cross-section in part of a portion of the assembly of the invention showing further valve means.

FIG. 1 is an isometric view a preferred embodiment assembly of the invention 10 shown in disassembly. The assembly 10 comprises a first needle cannula 12 which is adapted to puncture a mammalian blood vessel and carry blood therefrom into the bore 14 of a flexible tube 16. The needle 12 is connected to tube 16 by a cannula hub 18 within which it is mounted so as to leave its cutting edge 20 proximal to the first end 22 of hub 18 and distal to the end 24 of said hub 18. The diameter of tube 16 is selected so that it will make a frictional fit with the second end 24 of the hub 18, leaving the bore of needle 12 in open communication with bore 14 of tube 16. A needle shield 26 is preferably initially mounted on the end 22 of hub 18 to protect the needle 12 from contamination until it is required for use. The needle shield 26 is removably mounted so that it may easily be slipped off when it is desired to use the assembly 10 of the invention. The needle shield 26 advantageously falls short of covering the end 28 of tube 16.

Referring now to the opposite end 30 of tube 16 one may readily observe that this end is closed with a second needle cannula 32 and its mounting hub 34, one end 36 of which is inserted into the tube end 30. The other end 38 of hub 34 bears threads 40, the function of which will be discussed more fully hereinafter. Needle cannula 32 is adapted to penetrate a cannula penetrable closure in a sealed vacuum bottle, such as is conventionally employed for the collection of blood. A typical representative blood collection container 42 is shown in FIG. 1 and comprises a tubular form, closed at one end with a stopper 44 which is cannula penetrable. The other end of the container 42 is closed by a joining of the container sidewalls at point 46. Referring again to needle cannula 32, it will be observed that the penetration point 48 is proximal to end 38 and distal to end 36 of hub 34.

The final component of the assembly 10 shown in FIG. 1 is a holder which comprises a tubular member 50 having an open first end 52 for receiving the blood collection container 42 into the bore 54 of the tubular member 50. The other end 56 of tubular member 50 is closed and forms a hub part 58 having an axial bore 60 therethrough which provides communication between bore 54 and the outside of tubular member 50. The axial bore 60 bears threads 62 which are adapted to engage the threads 40 on end 38 of hub 34 so that the holder member 50 may be removably mounted on hub 34.

In a particularly preferred assembly of the invention, the tube 16 component is lined with a chemical 64 compound for treatment of the blood passing through bore 14. Such chemical compositions may be anti-coagulants such as heparin and the like. Any other chemical composition with which it is desired to treat the blood may also be coated on the walls of tube 16 defining the bore 14.

Referring now to FIG. 2, a cross-section view along lines 2—2 of FIG. 1, one may observe the lining of tube 16 with a chemical composition 64 such as heparin.

FIG. 3 is a cross-sectional side elevation showing the mounting of tubular member 50 upon hub 34 via the interengagement of threads 40, 62. As shown, the needle 32, which is mounted in hub 34 by adhesive means 66 (preferably an epoxy adhesive). The point 48 of needle cannula 32 is positioned within the bore 54 of member 50, proximal to the open end 52. The mounting of holder member 50 by engagement of threads 40, 62 to hub 34 is particularly advantageous in that it permits one to remove the holder member 50 and reuse it a plurality of times even though the remaining components of the assembly 10 may be disposed of after a single use. This is an economical advantage since the holder member 50 may be a significant cost of the total assembly 10. Prior hereto, holder members similar to holder member 50 were generally an integral part of any blood collection assembly and they could not therefore be reused.

FIG. 4 is an illustration of an alternate embodiment assembly of the invention. It differs from the assembly shown in FIG. 1 in that a valve member 70 has been inserted in the pathway between the bore 14 of tube 16 and the bore of needle 32 mounted in hub 34. The valve 70 is connected to tube 16 by insertion in the end 30. At its opposite end, valve 70 is connected to the hub 34 by an adapter 72. Those skilled in the art will appreciate that inclusion of valve 70 in the flow path of blood travelling between bore 14 and the bore of needle 32 is particularly advantageous should one wish to interrupt the flow of blood from the mammalian blood vessel to the blood collection container 42.

Referring now to FIG. 5, another alternate embodiment assembly 10 of the invention may be seen wherein a one-way flow valve 74 has been substituted for the valve 70 seen in FIG. 4. The one-way flow valve 74 component provides for a particularly preferred assembly 10 of the invention providing a safety or backflow barrier, preventing sample backflow from the assembly 10 and particularly from the blood collection container 42, to the patient or mammal from whom the blood has been collected.

Figure 6:
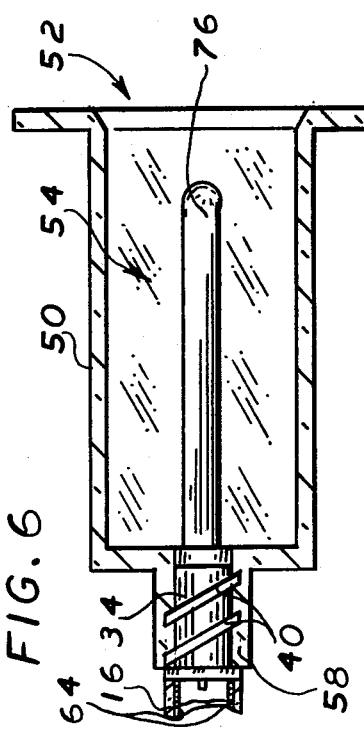
FIG. 6 is an isometric view of a preferred embodiment component in the assembly of the invention.
Figure 7:
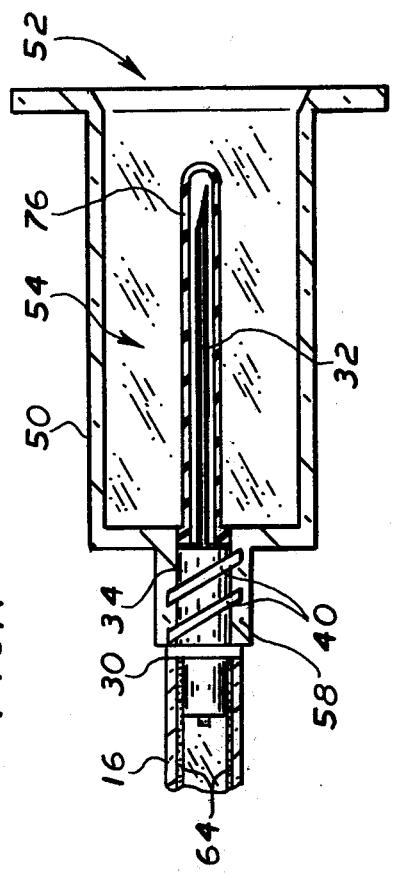
FIG. 7 is a cross-sectional side elevation of the embodiment shown in FIG. 6.

Referring now to FIG. 6, an isometric view of the the terminal portion of assembly 10, i.e.; of holder 50 one may see a further preferred embodiment assembly of the invention wherein the cannula 32 is masked with a flexible, cannula penetrable sheath 76. In FIG. 7, a cross-sectional side elevation of the embodiment seen in FIG. 6, one can see the enclosure of needle cannula 32 by the shield or sheath 76. The function of sheath 76 will be described more fully hereinafter in the discussion of operation of the assembly 10. The assembly 10 is operated as follows. The needle sheath 26 (see FIG. 8, a cross-sectional side elevation of sheath 26 mounted on needle 12) is removed and needle 12 is inserted into a mammalian blood vessel such as an artery or vein, following conventional techniques for venipuncture. In a most preferred embodiment apparatus 10 of the invention, the tube 16 is transparent so that the operator may immediately detect when he has entered a blood vessel, as evidenced by the slight flow of blood visible through the transparent walls of tube 16. (See FIG. 9 illustrating the puncture of blood vessel 80 by needle cannula 12, wherein there is a flow of blood 82 into the bore 14 of tube 16).

Referring now to FIG. 10, a cross-sectional side elevation of a portion of the tube 16 one may observe that in its flow towards the terminal end of the assembly 10, the blood 82 is treated by its contact with the chemical composition 64 lining the walls defining bore 14. If the chemical composition 64 is for example an anticoagulant, the blood 82 flowing through tube 16 will be treated to prevent clot formation.

If needle 32 were inserted through the cannula penetrable closure 44 of a blood container 42, which is positioned in the bore 54 of holder member 50, the blood would be delivered to the interior of the blood collection container 42. In the preferred embodiment described in FIGS. 6 and 7, and shown in FIG. 11, the blood would of necessity be contained within sheath 76 in the absence of insertion of subsequent blood collection containers 42 within bore 54 of the holder member 50. This is shown in FIG. 11. Control of blood flow out of the bore of needle cannula 32 would of course also be obtained in the preferred assembly 10 which includes a valve 70 and wherein said valve 70 is closed to stop the flow of blood. This may be desirable in certain instances, for example where a certain residence time of blood 82 is desired within the bore 14 of tube 16, for example where it is desired to treat the blood 82 for a longer period of time with the chemical composition 64. When the desired residence time has been obtained, one can open the valve 70 or in the instance wherein the blood is being contained by sheath 76, act as follows.

Referring to FIG. 12, one can see that the tubular blood collection container 42 has been partially inserted within the bore 54 of tubular member 50 and blood is being contained by the closed needle point 48 which is within the stopper 44. However, the flexible, elastic sheath 76 has been pushed rearward, allowing the needle cannula point 48 to penetrate the lower end of sheath 76, exposing it.

Referring to FIG. 13, a side elevation as seen in FIG. 12 but following complete penetration of the stopper 44 by needle 32 one may see that the needle point 48 is now free and blood 82 is permitted to flow from the bore 14 of tube 16, and through the bore of needle 32 into collection container 42. Upon withdrawal of container 42 from the bore 54 of holder member 50, the elastic sheath 76 will return to its initial position as seen in FIGS. 6 and 7, whereupon the assembly 10 at its terminal end is again closed, preventing spillage of blood. This occurs because the elastic shield 76 is constructed of a resilient, material the penetration of which is closed upon withdrawal of the needle point 48. In this manner, a single insertion of the needle 12 into a mammalian blood vessel may be used to fill a plurality of blood collection containers without interruption of the needle collection to the mammalian blood vessel.

Those skilled in the art will appreciate that many modifications may be made to the above described preferred embodiments of the invention without departing from the spirit and scope of the invention. For example, the component parts of the assembly 10 may be fabricated from any conventional materials giving the desired characteristics.

What is claimed is:

1. An assembly for the collection of blood from a mammalian blood vessel, which comprises;
    a first needle cannula adapted to puncture said vessel and carry blood therefrom;
    a first cannula hub having a first end and a second end, within which said needle cannula is mounted, the needle cutting edge being proximal to said first end and distal to said second end;
    a length of flexible tube having a first end and a second end, the first end of which is attached to the second end of said hub and the bore of said tube being in open communication with the bore of said needle cannula;
    a second cannula hub having a first end connected to the second end of said tube and a second end bearing threads;
    a second needle cannula adapted to penetrate a cannula penetrable closure in a sealed vacuum bottle for collecting blood, mounted in said second hub with the penetration point proximal to the second end of said second hub and distal to the first end of said second hub; and
    a holder which comprises a tubular member having an open first end adapted to receive a blood collection container and hold it and a closed second end formed with a hub, said holder hub having an axial bore therethrough communicating with the bore of said tubular member, said axial bore bearing threads adapted to engage the threads on a second end of said second cannula hub, said holder being removably mounted on the second end of the second cannula hub by the engagement of said threads.

2. The assembly of claim 1 which additionally comprises a needle shield protectively covering said first needle cannula.

3. An assembly according to claim 1 which additionally comprises a chemical composition for treating blood lining the interior walls of said tube.

4. The assembly of claim 1 wherein there is located a valve between said flexible tube and the second cannula hub, whereby flow therebetween may be opened and closed.

5. The assembly of claim 1 wherein a one-way valve is positioned between said tube and said second hub, whereby backflow is prevented.

6. The assembly of claim 1 wherein there is an elastic, cannula penetrable, reclosable shield mounted over the penetrating end of said second needle cannula.

* * * * *